United States Patent
Rey et al.

(10) Patent No.: US 8,053,573 B2
(45) Date of Patent: Nov. 8, 2011

(54) MONOMER 5, 6-DIPHENYL-1.2.4-TRAIZINIC DERIVATIVES AND THE USE THEREOF

(75) Inventors: Jérôme Rey, Castres (FR); Pascal Bordat, Mervilla (FR); Roger Tarroux, Toulouse (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 1321 days.

(21) Appl. No.: 11/579,341

(22) PCT Filed: May 4, 2005

(86) PCT No.: PCT/FR2005/001129
§ 371 (c)(1),
(2), (4) Date: Jan. 23, 2007

(87) PCT Pub. No.: WO2005/121108
PCT Pub. Date: Dec. 22, 2005

(65) Prior Publication Data
US 2008/0299055 A1    Dec. 4, 2008

(30) Foreign Application Priority Data
May 5, 2004    (FR) ..................... 04 04810

(51) Int. Cl.
*C07D 253/065*    (2006.01)
*C07D 253/07*    (2006.01)
*A61K 31/53*    (2006.01)
*A61K 8/49*    (2006.01)
*A61Q 5/12*    (2006.01)
*A61Q 17/04*    (2006.01)

(52) U.S. Cl. .................. 544/182; 424/70.9; 252/301.23
(58) Field of Classification Search .................. 544/182; 424/70.9; 252/301.23
See application file for complete search history.

(56) References Cited

U.S. PATENT DOCUMENTS

| 3,130,046 | A | * | 4/1964 | Schlesinger | .................. 430/76 |
| 3,211,729 | A | * | 10/1965 | Siegrist et al. | ................ 544/182 |
| 3,948,894 | A | * | 4/1976 | Lacefield | ..................... 544/182 |
| 3,989,831 | A | * | 11/1976 | Lacefield | ..................... 514/242 |
| 4,008,232 | A | * | 2/1977 | Lacefield | ..................... 544/112 |

FOREIGN PATENT DOCUMENTS

FR    2 477 873 A    9/1981
FR    2 803 194    7/2001

OTHER PUBLICATIONS

BE 615619; CA 58: 73401,1963(Caplus Abstract).*
G. Pitet, H. Cousse, G. Mouzin, Boll. Chim. Form, 1980, 119, 469.
C. Tuzun, M. Ogliaruso, E. I. Becker, Org. Syn, 1961, 41, 1-4.
E.C. Taylor, L.G. French, J. Org. Chem., 1989, 54, 1245-1249.
English Absract of FR 2477 873, (1981).

* cited by examiner

*Primary Examiner* — Venkataraman Balasubramanian
(74) *Attorney, Agent, or Firm* — Birch, Stewart, Kolasch & Birch, LLP

(57) ABSTRACT

The invention relates to the use of 5,6-diphenyl-1,2,4-triazinic compounds of general formula (I), wherein cycle penetrating bonds display an ortho, meta or para indifferent substitution position, identical or different R1 and R2 represent a hydrogen, fluoride, chloride or bromine atom, C1 to C12 linear or branched alkyl, C1 A C18 linear or branched hydroxy, alkoxy poly(ethoxy)-alkoxy with a C1 to C4 alkyl fragment and an ethoxy number ranging from 1 to 4, amino or mono or di-alkylamino with a C1 to C4 alkyl fragment group, R3 represents a chlorine atom, a hydroxy, amino, a phenyl possibly 1 to 3 times substituted by a hydroxy radical situated at least in a para or phenyl position possibly 1 to 3 times substituted in an ortho, meta or para position by a C1 to C12 alkoxy or cyano or alkymino group with a C1 to C7 alkyl fragment in the form of active sun filters or light-protective agents and to cosmetic composition containing said compounds.

9 Claims, 2 Drawing Sheets

MONOMER 5,6-DIPHENYL-1.2.4-TRAIZINIC DERIVATIVES AND THE USE THEREOF

Figure 1:
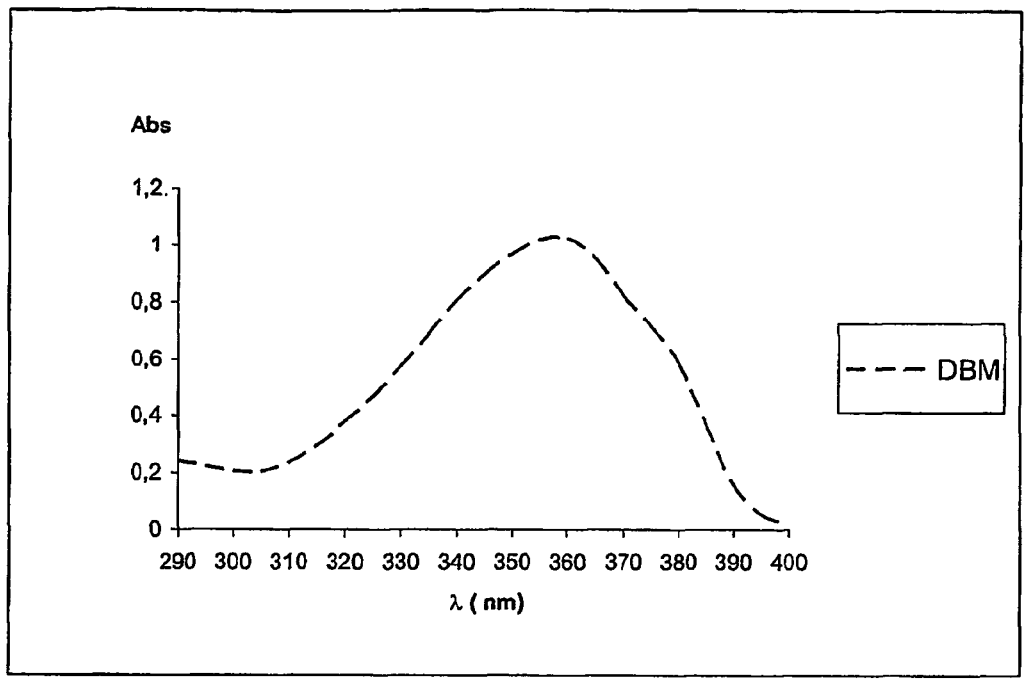

The present invention relates to 5,6-diphenyl-1,2,4-triazine derivatives, and in particular to the use thereof as sun filters on human skin and hair or as light-protective agents in the synthetic materials industry such as plastics, glass and textiles. The present invention also has as an object cosmetic compositions containing the aforesaid derivatives.

As a brief review, the action of solar radiation on the skin depends primarily on the energy of the radiation which reaches the various cutaneous layers. Generally speaking, the most energetic radiation, i.e., having the shortest wavelength ($E=hc/\lambda$), cause erythemas or "sunburn", whereas less energetic radiation only causes a simple browning of the skin. It is thus considered that a sun filter intended to be part of the composition of so-called "sunscreen" cosmetic preparations must absorb short wavelength radiation to the maximum degree possible while remaining transparent to radiation of longer wavelength.

Photobiologists typically divide the ultraviolet spectrum into three parts, called UV-A, UV-B and UV-C, which correspond to the decreasing wavelength ranges from 400 nm to 320 nm, from 320 nm to 280 nm and from 280 nm to 200 nm, respectively.

UV-B and UV-A allow the tanning of the human epidermis. UV-B causes erythemas and cutaneous burns which can harm the development of a natural tan. For these reasons, as well as for esthetic reasons, a constant demand exists for methods of controlling this natural tanning with a view to controlling the color of the skin. It is thus advisable to filter this UV-B radiation.

It is also known that UV-A rays are likely to induce a deterioration of the skin, in particular in the case of sensitive skin or skin continuously exposed to sun radiation. In particular, UV-A rays cause a loss of skin elasticity and the appearance of wrinkles which lead to premature aging. They cause the triggering of the erythematous reaction or amplify this reaction in certain subjects and can even be the cause of phototoxic or photoallergic reactions. It is thus desirable to UV filter-A radiation as well.

UV-C, which is the most highly energetic, causes photokeratitis. The ozone formed in the stratosphere generally absorbs a large part of this UV-C radiation which, on the other hand, is found in large amounts in the radiation emitted by artificial lamps, which are often responsible for serious cutaneous injuries. UV-B, which penetrates the skin layer and, in particular, the stratum mucosum of the epidermis, causes solar erythemas. Consequently, UV-B and UV-C radiation together constitute the so-called erythema spectrum with regard to which sun filters must act as a screen. UV-A produces the direct pigmentation of the skin (melanogenesis), i.e., the tanning of the skin.

Compounds derived from the benzotriazoles and/or the benzotriazoles are known as UV filters, in particular in the field of cosmetics. The patent application FR 2,803,194 thus disclosed S-triazine derivatives carrying phenylbenzothiazole or benzothiazole groups useful as UV filters in particulate form. These compounds cover the range of UV-A and of UV-B but they exhibit the major disadvantage of absorbing in the visible spectrum (wavelengths longer than 400 nm). Thus these products are heavily colored, which limits their use in cosmetic products.

The present invention proposes novel 5,6-diphenyl-1,2,4-triazine derivatives capable of absorbing in UV-A and/or UV-B and/or UV-C, without absorbing in the visible spectrum. Thus these compounds have the advantage of being lightly colored.

They also have the advantage of being capable of being specific to one of these spectra. This is advantageous when it is desired to filter a specific UV spectra (UV-A, UV-B or UV-C), for example to supplement the spectral effectiveness of a UV filter which exhibits a gap in this specific range.

These novel derivatives thus offer a varied range of specific UV filters which can also exhibit various degrees of absorbance. The combination of several of these filters selected according to their specificity and their degree of absorbance thus makes it possible to prepare all types of UV filters acting in the spectrum and with the absorbance desired.

These novel derivatives also have the advantage of being soluble in various pharmaceutically acceptable excipients and of exhibiting better photostability than certain commercial filters, which makes them particularly useful in cosmetic products, notably in sun protectors.

The present invention has as an object the use, as sun filters active in UV-A and/or UV-B and/or UV-C for human skin and/or hair, of 5,6-diphenyl-1,2,4-triazinic compounds of general formula (I):

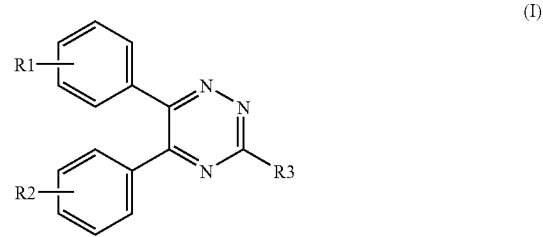

wherein:
the bonds that penetrate into the ring indicate an indifferent substitution position of ortho, meta or para,
$R_1$ and $R_2$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment,
$R_3$ represents a chlorine atom, a hydroxy group, an amino group, a phenyl group possibly substituted 1 to 3 times with a hydroxy radical located at least in para position, a phenyl group possibly substituted 1 to 3 times in ortho, meta or para position with a $C_1$ to $C_{12}$ alkoxy or a cyano and an alkylimino group with a $C_1$ to $C_7$ alkyl fragment.

The present invention also has as an object the use of compounds such as previously defined as light-protective agents active in the UV-A and/or UV-B and/or UV-C spectra, useful in the synthetic materials industry, in particular as light-protective agents incorporated into the composition of plastics, glass or textiles.

These compounds, which are objects of the present invention, can thus be used to protect photosensitive materials.

The light-protective agent could be incorporated into a substratum with the goal of protecting said substratum against attack from ultraviolet rays, to prevent the modification of one or several physical properties of said substratum, such as, for example, discoloration, a change in resistance to tearing, an increase in brittleness, etc., and/or to prevent chemical reactions caused by ultraviolet rays, for example the oxidation process. In this case, the protective agent can be incorporated before and during the preparation of the substratum, or at a later time by a suitable process, for example a binding process analogous to dyeing.

The light-protective agent can also be incorporated into a substratum to protect one or more additional substances incorporated into the aforesaid substratum, for example dyes, auxiliary agents, etc.

The light-protective agent can also be incorporated into a filter layer that may be a solid (film, sheet) or semi-solid (cream, oil, wax) applied to a substratum for the purpose of protecting said substratum from ultraviolet rays.

The compounds of the present invention are suitable not only as light-protective agents for colorless materials, but also for pigmented materials. In this case, the protection against light is extended to the coloring agents, thus allowing in many cases a quite notable improvement of stability in light.

The present invention also has as an object the 5,6-diphenyl-1,2,4-triazinic compounds of general formula (Ia):

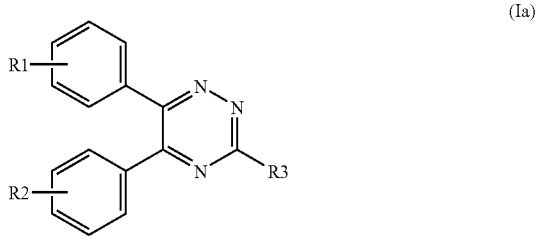

wherein:
  $R_1$ and $R_2$ represent a $CH_3O$— group, and
  $R_3$ represents:
    a phenyl group substituted one or several times by a hydroxy radical located at least in para position,
    a phenyl group substituted in ortho, meta or para position by a radical chosen among an alkoxy at $C_1$ or $C_{12}$ or a cyano,
    or an alkylimino group with an alkyl fragment at $C_1$ to $C_7$.

Among the compounds of general formula (Ia), the following compounds have led to particularly advantageous practical results:
  $R_1$ and $R_2$ representing a $CH_3O$— group located in para position, and
  $R_3$ representing a phenyl group substituted with a hydroxy radical in para position, or by a cyano or an alkoxy at $C_1$ to $C_{12}$ in ortho, meta or para position.

The present invention also has as an object cosmetic sunscreen compositions containing an effective quantity of at least one compound of formula (Ia) in combination with a cosmetically acceptable excipient, preferably between 0.1% and 20% by weight with respect to the total weight of the composition.

The cosmetic sunscreen compositions according to the invention may contain in addition one or more sun filters active in UV-A and/or UV-B and/or UV-C (absorbers), either hydrophilic or lipophilic. These additional filters may be selected among, in particular, cinnamic derivatives, dibenzoylmethane derivatives, salicylic derivatives, camphor derivatives and triazine derivatives other than those previously cited in the present invention.

The compounds of general formula (I) can be prepared from 1,2-diketones of formula (II), by conventional methods known to those skilled in the art, such as those described in the examples which follow.

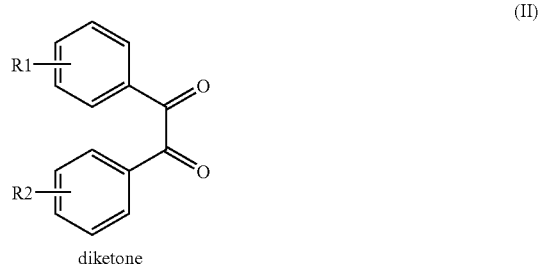

in which $R_1$ and $R_2$ have the same significance as that given previously.

The diketones of formula (II) are available commercially (such as, for example, benzyl(diphenylethan-1,2-dione), 4,4'-dimethylbenzyl, 4,4'-dibromobenzyl, 4,4'-difluorobenzyl or 4,4'-dichlorobenzyl) or can be synthesized by conventional methods well known to those skilled in the art. For example, the following synthesis route can be used:

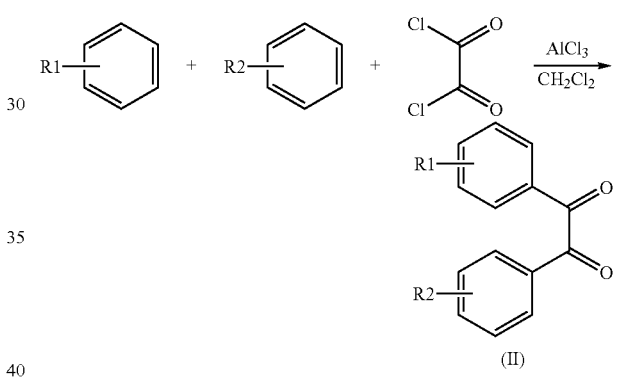

The examples which follow give other examples of syntheses of diketones of formula (II).

The present invention will be illustrated below by mentioning several nonrestrictive examples of the preparation of representative derivatives conforming to general formula (I).

The compounds prepared are summarized in table 1.

TABLE I (I)

(wherein $R_1$ and $R_2$ are in the para position)

| Reference | $R_1, R_2$ | $R_3$ |
|---|---|---|
| JR18 | —N(Et)$_2$ | —OH |
| JR63 | —OMe | -Ph |
| JR65 | —OMe | -Ph(OH)p |
| JR67 | —H | -Ph(OH)o |

TABLE I-continued (I)

(wherein $R_1$ and $R_2$ are in the para position)

| Reference | $R_1, R_2$ | $R_3$ |
|---|---|---|
| JR68 | —H | -Ph(OH)p |
| JR70 | —OMe | -Ph(OMe)p |
| JR77 | —OMe | —$NH_2$ |
| JR89 | —OMe | -Ph(OH)o |
| JR98 | —OMe | —Cl |
| JR99 | —OMe | —OH |
| JR106 | —H | —$NH_2$ |
| JR107 | —OMe | -Ph(CN)p |
| JR113 | —OMe | -Ph(CN)m |
| JR114 | —OMe | -Ph(CN)o |
| JR115 | —OMe | -Ph(OH)$_3$ |
| JR117 | —OMe | —$NCH(CH_2)_5CH_3$ |
| JR144 | —H | -Ph(CN)m |
| JR145 | —H | -Ph(CN)o |
| JR173 | —OMe | -Ph(OC$_{12}$H$_{25}$)p |

The compounds of formula (I) of table 1 can be synthesized in the following way:

(II)

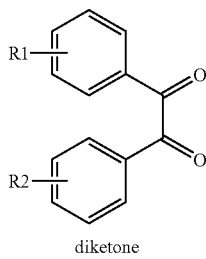

diketone wherein $R_1, R_2$=
 hydrogen, halogen,
 —OH,
 $C_1$ to $C_{18}$ linear or branched alkoxy (such as —OMe)
 —$C_1$ to $C_{12}$ linear or branched alkyl,
 mono- or di-alkylamino with a $C_1$ to $C_4$ alkyl fragment (such as —$N(Et)_2$).

diketone (II)

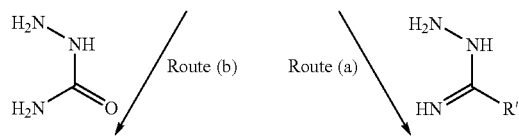

JR 98
JR 99
JR 18

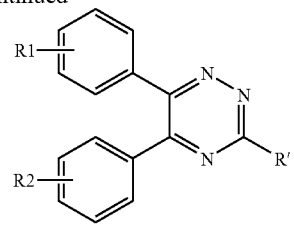

wherein R'=chlorine,
 amino,
 —OH,
 phenyl possibly substituted 1 to 3 times with a —OH radical located in at least para position,
 phenyl possibly substituted 1 to 3 times in ortho, meta or para position with a radical chosen among an alkoxy at $C_1$ to $C_{12}$ (such as —OMe or —$OC_{12}H_{25}$) or a cyano,
 alkylamino with an alkyl fragment at $C_1$ to $C_7$ (such as —$NCH(CH_2)_5CH_3$).

FIGURES

Figure 2:
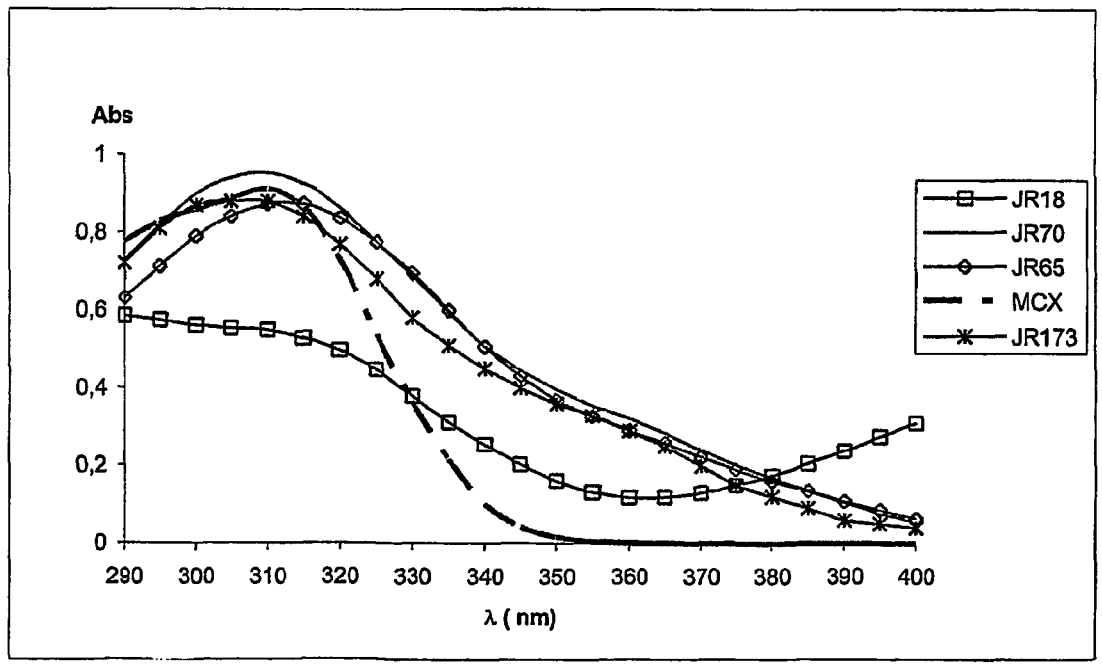
Figure 3:
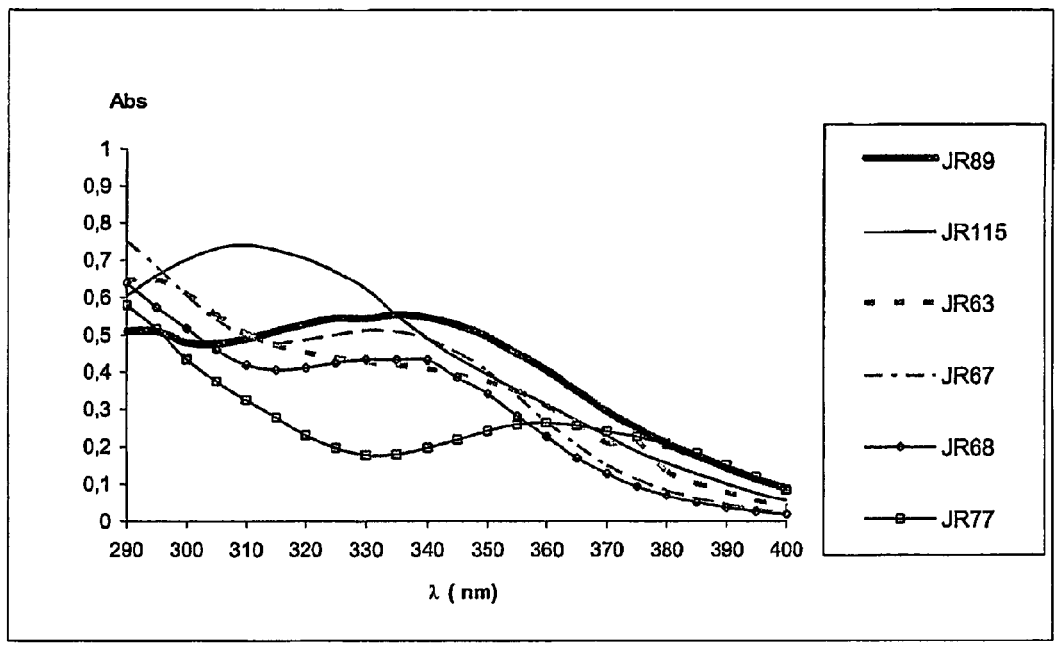
Figure 4:
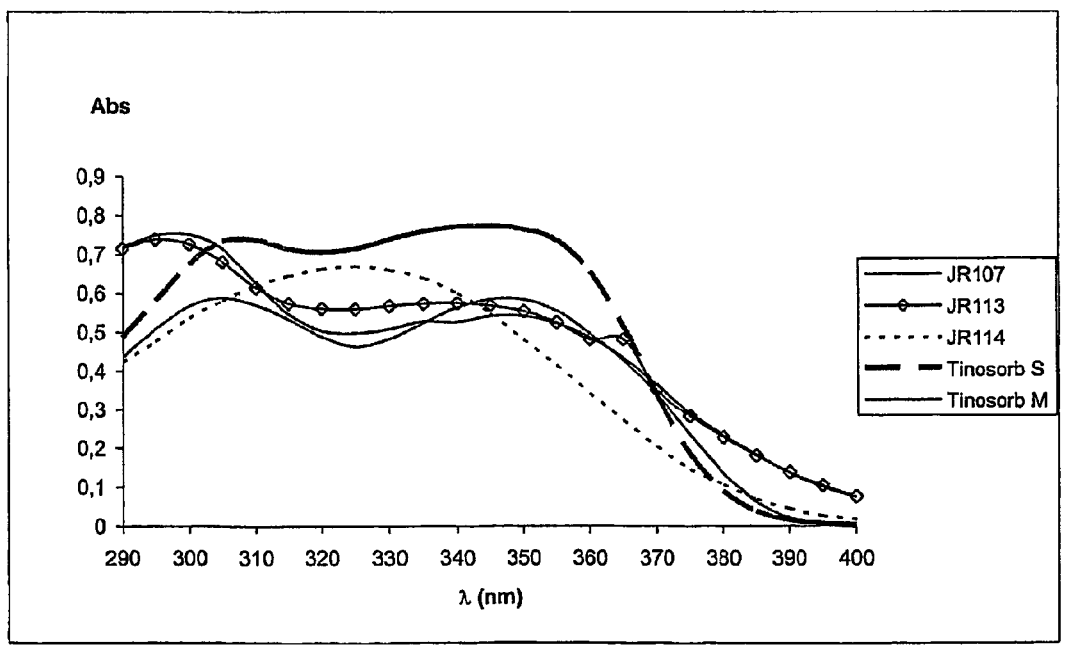

DBM=Parsol 1789® (Roche Laboratories)
MCX=Parsol MCX® (Roche Laboratories)
FIG. 1 represents the UV-A and UV-B absorption spectra of Parsol 1789®.
FIG. 2 represents the UV-A and UV-B absorption spectra of compounds JR18, JR70 and JR65 in comparison with that of Parsol MCX®.
FIG. 3 represents the UV-A and UV-B absorption spectra of compounds JR89, JR115, JR63, JR67, JR68 and JR77.
FIG. 4 represents the UV-A and UV-B absorption spectra of compounds JR107, JR113 and JR114 in comparison with those of Tinsorb S® and Tinsorb M®.

EXAMPLE 1

Synthesis of 1,2-bis(4-methoxyphenyl)-ethane-1,2-dione[1]

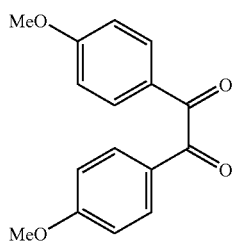

$C_{16}H_{14}O_4$ M=270.28 g/mol

Oxalyl chloride (4.71 ml, 55.2 mmol) at 0° C. is slowly added to a mixture of anisole (10.8 g, 100 mmol) and aluminum chloride (33.33 g, 250 mmol). The mixture is stirred at ambient temperature for 4 hours. After cooling, it is poured into iced water and extracted with dichloromethane. The organic phases collected are washed with 2 N HCl then with brine and are dried on magnesium sulfate. After filtration and concentration under reduced pressure, the residue is recrystallized in ethanol. The resulting precipitate is filtered, washed several times in ethanol and dried to yield 9.80 g (66%) of pure product in the form of a yellow solid. $\delta_H$ (200 MHz, CDCl$_3$) 3.93 (s; 6H), 6.99 (d; J 7.8; 4H), 7.99 (d; J 7.8; 4H).

EXAMPLE 2

Synthesis of 1,2-bis(4-diethylaminophenyl)-ethane-1,2-dione[(2)]

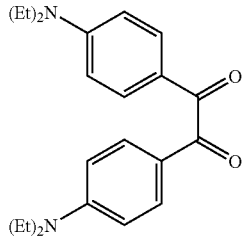

$C_{22}H_{28}N_2O_2$ M=352.48 g/mol

Oxalyl chloride (44.1 ml, 191.1 mmol) at 0° C. is slowly added to a mixture of N,N'-diethylaniline (60 g, 382.1 mmol) and aluminum chloride (30.57 g, 229.3 mmol). The mixture is stirred at ambient temperature for 4 hours. After cooling, it is poured into iced water and extracted with dichloromethane. The recombined organic phases are washed with 2 N HCl then with brine and are dried on magnesium sulfate. After filtration and concentration under reduced pressure, the residue is recrystallized in ethanol. The resulting precipitate is filtered, washed several times with ethanol and dried to yield 13.55 g (70%) of pure product in the form of a yellow solid. $\delta_H$ (200 MHz, CDCl$_3$), 1.25 (t; 12H), 3.45 (q; 8H), 6.65 (d; J 7.8; 4H), 7.87 (d; J 7.8; 4H).

EXAMPLE 3

Synthesis of 3-hydroxy-5,6-bis(4-diethylaminophenyl)-1,2,4-triazine (JR18)

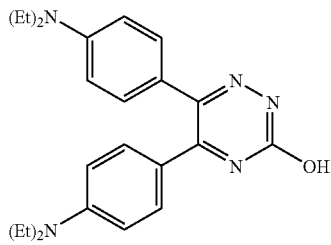

$C_{22}H_{29}N_5O$ M=391.52 g/mol

Semicarbazide hydrochloride (1.57 g, 14.2 mmol) and sodium acetate (1.41 g, 17.3 mmol) are added to a solution of 1,2-bis(4-diethylaminophenyl)-ethane-1,2-dione prepared according to example 2 (5 g, 14.2 mmol) in acetic acid (20 ml). The mixture is heated at reflux for 12 hours. After returning to ambient temperature, the reaction mixture is poured into water. The raw solid is collected by filtration and washed with water. The residue is recrystallized in acetic acid. After filtration and washing with water, 3 g (54%) of a yellow solid are obtained after drying. $\delta_H$ (200 MHz, CDCl$_3$), 1.18 (t; 12H), 3.45 (q; 8H), 6.65 (d; J 7.8; 4H), 7.87 (d; J 7.8; 4H), 10.4 (s; 1H)

EXAMPLE 4

Synthesis of 3-(2-hydroxyphenyl)-5,6-bis(4-methoxyphenyl)-1,2,4-triazine (JR89)

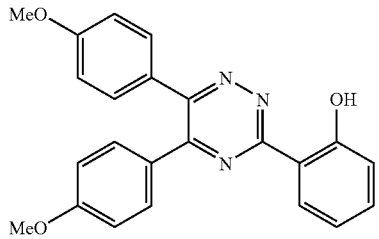

$C_{23}H_{19}N_3O_3$ M=385.42 g/mol

2-Hydroxyphenylhydrazide (2.23 g, 14.8 mmol) is added to a solution of 1,2-bis(4-methoxyphenyl)-ethane-1,2-dione prepared according to example 1 (4 mg, 14.8 mmol) in acetic acid (20 ml) in the presence of ammonium acetate. The mixture is heated at reflux for 5 hours. After returning to ambient temperature, the precipitate obtained is filtered, successively washed with acetic acid then with ethanol and is dried to yield a yellow solid. The residue is recrystallized in a dimethylformamide/ethanol mixture (95/5) to yield 2.90 g (51%) of a yellow solid. $\delta_H$ (200 MHz, CDCl$_3$), 3.86 (s; 6H), 7.02 (m; 4H), 7.58 (d; J 7,8; 2H), 7.71 (m; 4H), 8.77 (d; J 8.7; 2H), 12.3 (s; 1H); MS (Electrospray) m/z 386 (MH$^+$, 100%).

EXAMPLE 5

Synthesis of 3-(4-hydroxyphenyl)-5,6-bis(4-methoxyphenyl)-1,2,4-triazine (JR65)

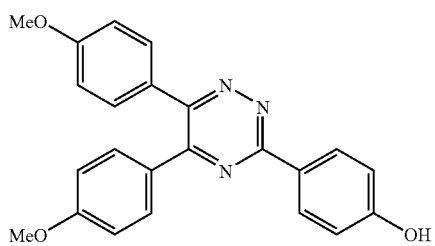

$C_{23}H_{19}N_3O_3$ M=385.42 g/mol

4-Hydroxyphenylhydrazide (2.23 g, 14.8 mmol) is added to a solution of 1,2-bis(4-methoxyphenyl)-ethane-1,2-dione prepared according to example 1 (4 mg, 14.8 mmol) in acetic acid (20 ml) in the presence of ammonium acetate. The mixture is heated at reflux for 6 hours. After returning to ambient temperature, the precipitate obtained is filtered, successively washed with acetic acid then with ethanol and is dried to yield a yellow solid. The residue is purified by chromatography on a silica gel (dichloromethane/ethanol: 95/5) to yield 2.56 g (45%) of a yellow solid. $\delta_H$ (200 MHz, CDCl$_3$), 3.86 (s; 6H), 7.02 (m; 4H), 7.58 (d; J 7.8; 2H), 7.71 (m; 4H), 8.77 (d; J 8.7; 2H), 11.79 (s; 1H); MS (Electrospray) m/z 386 (MH$^+$; 100%).

EXAMPLE 6

Synthesis of 3-(2-hydroxyphenyl)-5,6-diphenyl-1,2,4-triazine (JR67)

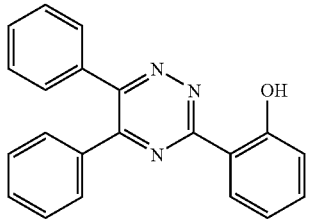

$C_{21}H_{15}N_3O$ M=325.37 g/mol

2-Hydroxyphenylhydrazide (3.17 g, 20.9 mmol) is added to a solution of benzyl (4 mg, 19 mmol) in acetic acid (20 ml) in the presence of ammonium acetate. The mixture is heated at reflux for 4.5 hours. After returning to ambient temperature, the precipitate obtained is filtered, successively washed with acetic acid then with ethanol and is dried to yield a yellow solid. The residue is recrystallized in a dimethylformamide/ethanol mixture (90/10) to yield 3.15 g (51%) of a yellow solid. $\delta_H$ (200 MHz, CDCl$_3$), 7.02 (m; 5H), 7.58 (d; J 7.8; 2H), 7.71 (m; 4H), 8.77 (d; J 8.7; 2H), 12.6 (s; 1H); MS (Electrospray) m/z 359 (MH$^+$; 100%), 673 (2M+Na$^+$; 21%).

EXAMPLE 7

Synthesis of 3-(4-hydroxyphenyl)-5,6-diphenyl-1,2,4-triazine (JR68)

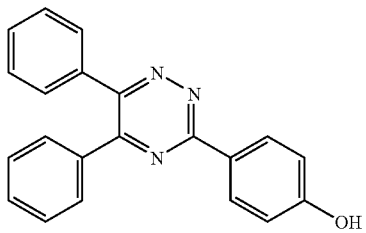

$C_{21}H_{15}N_3O$ M=325.37 g/mol

4-Hydroxyphenylhydrazide (3.17 g, 20.9 mmol) is added to a solution of benzyl (4 mg, 19 mmol) in acetic acid (20 ml) in the presence of ammonium acetate. The mixture is heated at reflux for 3 hours. After returning to ambient temperature, the precipitate obtained is filtered, successively washed with acetic acid then with ethanol and is dried to yield a yellow solid. The residue is purified by chromatography on a silica gel (dichloromethane/ethanol: 94/6) to yield 3.46 g (56%) of a yellow solid. $\delta_H$ (200 MHz, CDCl$_3$), 7.02 (m; 5H), 7.58 (d; J 7.8; 2H), 7.71 (m; 4H), 8.77 (d; J 8.7; 2H), 11.79 (s; 1H); MS (Electrospray) m/z 326 (MH$^+$, 100%).

EXAMPLE 8

Synthesis of 3-(4-methoxyphenyl)-5,6-bis(4-methoxyphenyl)-1,2,4-triazine (JR70)

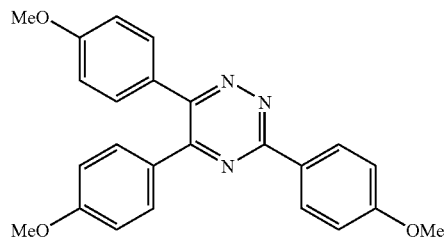

$C_{24}H_{21}N_3O_3$ M=399.45 g/mol

4-Methoxyphenylhydrazide (2.23 g, 14.8 mmol) is added to a solution of 1,2-bis(4-methoxyphenyl)-ethane-1,2-dione prepared according to example 1 (4 g, 14.8 mmol) in acetic acid (20 ml) in the presence of ammonium acetate. The mixture is heated at reflux for 5 hours. After returning to ambient temperature, the precipitate obtained is filtered, successively washed with acetic acid then with ethanol and is dried to yield a yellow solid. The residue is purified by chromatography on a silica gel (dichloromethane/ethanol: 95/5) to yield 2.42 g (41%) of a yellow solid. $\delta_H$ (200 MHz, CDCl$_3$), 3.86 (s; 6H), 3.90 (s; 3H), 7.02 (m; 4H), 7.58 (d; J 7.8; 2H), 7.71 (m; 4H), 8.63 (d; J 8.7; 2H); MS (Electrospray) m/z 460 (MH$^+$, 100%).

EXAMPLE 9

Synthesis of 3-(3,4,5-hydroxyphenyl)-5,6-bis(4-methoxyphenyl)-1,2,4-triazine (JR115)

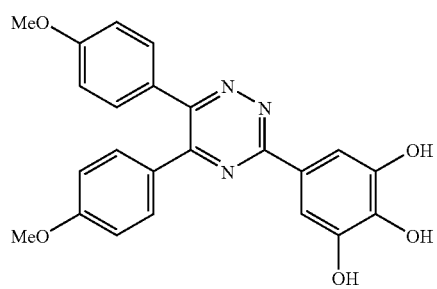

$C_{23}H_{19}N_3O_5$ M=417.42 g/mol 3,4,5-Trihydroxyphenylhydrazide (2.5 g, 11 mmol) is added to a solution of 1,2-bis(4-methoxyphenyl)-ethane-1,2-dione prepared according to example 1 (3 g, 11 mmol) in acetic acid (20 ml) in the presence of ammonium acetate. The mixture is heated at reflux for 5.5 hours. After returning to ambient temperature, the precipitate obtained is filtered, successively washed with acetic acid then with ethanol and is dried to yield a yellow solid. The residue is purified by chromatography on a silica gel (dichloromethane/ethanol 90/10) to yield 200 mg (5%) of a yellow solid. $\delta_H$ (200 MHz, CDCl$_3$, 3.86 (s; 6H), 7.02 (m; 4H), 7.58 (d; J 7.8; 2H), 7.71 (d; J 8.7;

2H), 8.70 (5; 2H), 7.71 (m; 4H), 8.77 (d; J 8.7; 2H), 11.79 (s; 1H), 11.90 (2H; s); MS (Electrospray) m/z 418 (MH⁺, 100%).

EXAMPLE 10

Synthesis of 3-(4-dodecyloxyphenyl)-5,6-bis(4-methoxyphenyl)-1,2,4-triazine (JR173)

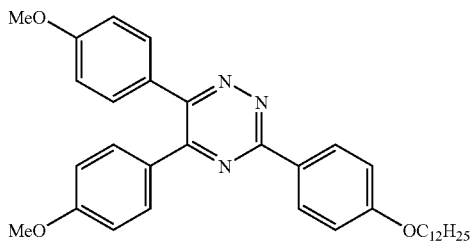

$C_{35}H_{43}N_3O_3$ M=553.74 g/mol

JR65 (7 g, 18.1 mmol) prepared according to example 5 is added to a solution of sodium hydroxide (872 mg, 21.8 mmol) in ethanol (50 ml). The mixture is stirred for half an hour. 1-Bromododecane (9.473 g, 38 mmol) is added to the solution. The whole is brought to reflux in ethanol for 12 hours. After returning to ambient temperature, the precipitate obtained is filtered and recrystallized twice in cyclohexane to yield 5.2 g (52%) of a yellow solid. $\delta_H$ (200 MHz, CDCl₃), 0.92 (m; 3H), 1.20-1.40 (m; 19H), 1.50-1.87 (m; 2H), 3.91 (s; 6H), 4.00 (t; J 7.5, 2H) 6.95 (m; 4H), 7.65 (d; J 7.8; 2H), 7.82 (m; 4H), 8.63 (d; J 8.7; 2H); MS (Electrospray) m/z 554 (MH⁺, 100%).

EXAMPLE 11

Synthesis of 3-amino-5,6-bis(4-methoxyphenyl)-1,2,4-triazine (JR77)

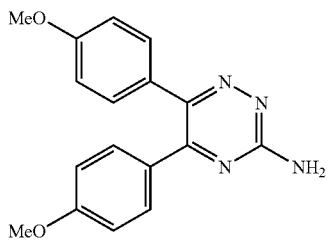

$C_{17}H_{16}N_4O_2$ M=308.34 g/mol

Aminoguanidine (2.450 g, 2.21 mmol) is added to a solution of 1,2-bis(4-methoxyphenyl)-ethane-1,2-dione preparedaccording to example 1 (5 g, 18.5 mmol) in ethanol (50 ml). The mixture is heated at reflux for 12 hours. After returning to ambient temperature, the precipitate obtained is filtered, washed with ethanol and is dried to yield a yellow solid. The residue is purified by chromatography on a silica gel (dichloromethane/triethylamine 0.5%) to yield 3.7 g (65%) of a yellow solid. $\delta_H$ (200 MHz, CDCl₃), 3.88 (s; 6H), 5.51 (s; 2H), 6.92 (m; 4H), 7.41 (m; 4H).

EXAMPLE 12

Synthesis of [5,6-bis(4-methoxyphenyl)-[1,2,4]-triazin-3-yl]heptylidine-amine (JR117)

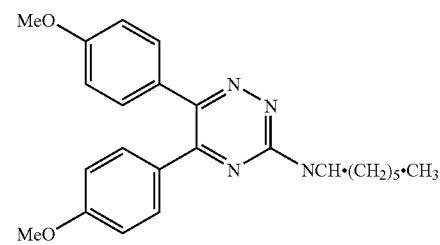

$C_{24}H_{28}N_4O_2$ M=404.50 g/mol

JR77 prepared according to example 11 (2 g, 6.5 mmol) and heptaldehyde (0.907 ml, 6.5 mmol) are placed in solution in glacial acetic acid and heated at reflux for 1.5 hours. After cooling, the raw reaction product is precipitated on crushed ice. The solid obtained is placed in solution in dichloromethane and filtered. The solvent is evaporated dry, 2 g of a yellow oil are obtained. $\delta_H$ (200 MHz, CDCl₃), 0.92 (m; 3H), 1.29 (m; 6H), 1.59 (m; 2H), 2.34 (t; J 7.5, 2H) 3.86 (s; 6H), 6.77 (d; 2H) 6.89 (d; 2H), 7.44 (m; 4H); MS (Electrospray) m/z 405 (MH⁺, 100%).

EXAMPLE 13

Synthesis of 2-cyanophenylcarboxamidehydrazone

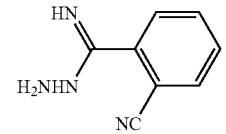

$C_8H_8N_4$ M=160.18 g/mol

A mixture of 1,2-dicyanobenzene (10 g, 78.1 mmol) and hydrazine monohydrate (50 ml) is placed under a nitrogen atmosphere. The mixture is stirred at ambient temperature for 12 hours. The yellow precipitate obtained is then filtered and placed in ethanol to recrystallize to yield 5 g (40%) of a yellow solid. $\delta_H$ (200 MHz, acetone-d), 3.53 (m; 4H), 7.72 (m; 1H), 8.05 (m; 2H), 8.58 (s; 1H).

EXAMPLE 14

Synthesis of 3-cyanophenylcarboxamidehydrazone

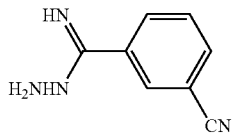

$C_8H_8N_4$ M=160.18 g/mol

A mixture of 1,3-dicyanobenzene (10 g, 78.1 mmol) and hydrazine monohydrate (50 ml) is placed under a nitrogen atmosphere. The mixture is stirred at ambient temperature for 12 hours. The yellow precipitate obtained is then filtered and placed in ethanol to recrystallize to yield 5.62 g (45%) of a yellow solid. $\delta_H$ (200 MHz, CDCl$_3$), 3.53 (m; 4H), 7.50 (t; J 7.3; 1H), 7.67 (d; J 7.3; 2H), 7.95 (m; 1H).

EXAMPLE 15

Synthesis of 4-cyanophenylamidrazone

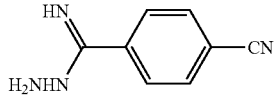

$C_8H_8N_4$ M=160.18 g/mol

A mixture of 1,4-dicyanobenzene (10 g, 78.1 mmol) and hydrazine monohydrate (50 ml) is placed under a nitrogen atmosphere. The mixture is stirred at ambient temperature for 12 hours. The yellow precipitate obtained is then filtered and placed in ethanol to recrystallize to yield 5.75 g (46%) of a yellow solid. $\delta_H$ (200 MHz, CDCl$_3$) 3.51 (m; 4H) 7.70 (d; J 7.3; 2H), 7.95 (J; 7.3; 2H).

EXAMPLE 16

Synthesis of 3-(3-cyanophenyl)-5,6-diphenyl-1,2,4-triazine (JR144)

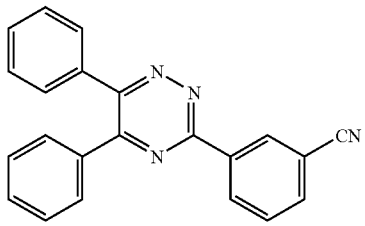

$C_{22}H_{14}H_4$ M=334.00 g/mol

3-Cyanophenylcarboxamidehydrazone (1 g, 6.25 mmol) prepared according to example 14 is added to a solution of benzyl (2.14 g, 10.2 mmol) in dimethylsulfoxide (DMSO) (100 ml). The mixture is heated at reflux for 15.5 hours at 130° C. After returning to ambient temperature, the raw reaction product is precipitated in water, the precipitate obtained is filtered and then dried. The residue is purified by chromatography on a silica gel (dichloromethane) to yield 1.2 g (57%) of a yellow solid. $\delta_H$ (200 MHz, CDCl$_3$), 7.35 (m; 5H), 7.65 (d; J 7.8; 2H), 7.82 (d; J 8.7; 2H), 8.63 (s; 4H); MS (Electrospray) m/z 335 (MH$^+$, 100%).

EXAMPLE 17

Synthesis of 3-(2-cyanophenyl)-5,6-diphenyl-1,2,4-triazine (JR145)

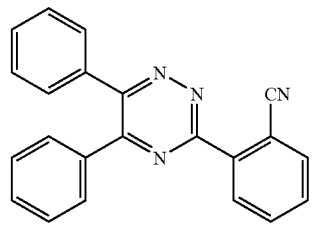

$C_{22}H_{14}N_4$ M=334.00 g/mol

2-Cyanophenylcarboxamidehydrazone (1 g, 6.25 mmol) prepared according to example 13 is added to a solution of benzyl (2.142 g, 10.2 mmol) in dimethylsulfoxide (DMSO) (100 ml). The mixture is heated at reflux for 15.5 hours at 130° C. After returning to ambient temperature, the raw reaction product is precipitated in water, the precipitate obtained is filtered and then dried. The residue is purified by chromatography on a silica gel (dichloromethane) to yield 1.1 g (55%) of a yellow solid. $\delta_H$ (200 MHz, CDCl$_3$), 7.34 (m; 5H), 7.65 (m; 3H), 7.82 (s; 1H), 8.63 (s; 4H); MS (Electrospray) m/z 335 (MH$^+$, 100%).

EXAMPLE 18

Synthesis of 3-(2-cyanophenyl)-5,6-bis(4-methoxyphenyl)-1,2,4-triazine (JR114)

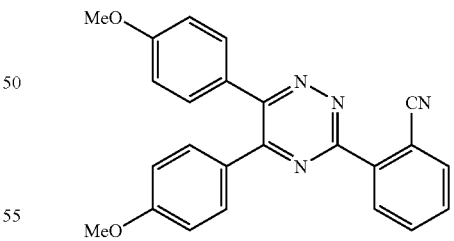

$C_{24}H_{18}N_4O_2$ M=394.43 g/mol

2-Cyanophenylcarboxamidehydrazone (1 g, 6.25 mmol) prepared according to example 13 is added to a solution of 1,2-bis(4-methoxyphenyl)-ethane-1,2-dione (2.75 g, 10.2 mmol) prepared according to example 1 in ethanol (20 ml). The mixture is heated at reflux for 9.5 hours. After returning to ambient temperature, the solvent is evaporated and the solid is purified by chromatography on a silica gel (dichloromethane/ethanol: 95/5). 1.653 g (40%) of an orange yellow product is obtained. $\delta_H$ (200 MHz, CDCl$_3$), 3.86 (s; 6H), 6.88

(m; 4H), 7.58 (d; J 7.8; 2H), 7.82 (m; 4H), 8.77 (d; J 8.7; 2H); MS (Electrospray) m/z 395 (MH+, 100%).

EXAMPLE 19

Synthesis of 3-(3-cyanophenyl)-5,6-bis(4-methoxyphenyl)-1,2,4-triazine (JR113)

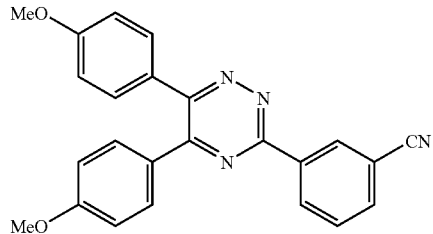

$C_{24}H_{18}N_4O_2$ M=394.43 g/mol

3-Cyanophenylcarboxamidehydrazone (1.5 g, 9.37 mmol) prepared according to example 14 is added to a solution of 1,2-bis(4-methoxyphenyl)-ethane-1,2-dione (4.2 g, 15.6 mmol) prepared according to example 1 in ethanol (20 ml). The mixture is heated at reflux for 10 hours. After returning to ambient temperature, the solvent is evaporated and the solid is purified by chromatography on a silica gel (dichloromethane/ethanol: 96/4). After evaporation of the solvent, 963 mg (37%) of a yellow solid are obtained. $\delta_H$ (200 MHz, CDCl$_3$), 3.91 (s; 6H), 6.95 (m; 4H), 7.65 (m; 3H), 7.82 (m; 4H), 8.63 (m; 2H); MS (Electrospray) m/z 395 (MH+, 100%).

EXAMPLE 20

Synthesis of 3-(4-cyanophenyl)-5,6-bis(4-methoxyphenyl)-1,2,4-triazine (JR107)

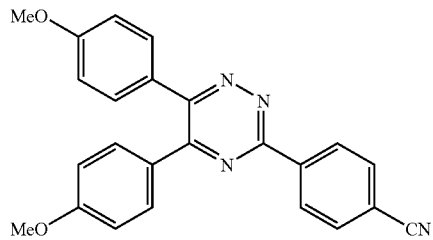

$C_{24}H_{18}N_4O_2$ M=394.43 g/mol

4-Cyanophenylcarboxamidehydrazone (1 g, 6.25 mmol) prepared according to example 15 is added to a solution of 1,2-bis(4-methoxyphenyl)-ethane-1,2-dione (2.81 g, 10.41 mmol) prepared according to example 1 in ethanol (20 ml). The mixture is heated at reflux for 12 hours. After returning to ambient temperature, the solvent is evaporated and the solid is purified by chromatography on a silica gel (dichloromethane/ethanol: 96/4). After evaporation of the solvent, 1.92 g (78%) of a yellow solid is obtained. $\delta_H$ (200 MHz, CDCl$_3$), 3.91 (s; 6H), 6.95 (m; 4H), 7.65 (d; J 7.8; 2H), 7.82 (m; 4H), 8.63 (d; J 8.7; 2H); MS (Electrospray) m/z 395 (MH+, 100%).

EXAMPLE 21

Synthesis of 3-hydroxy-5,6-bis(4-methoxyphenyl)-1,2,4-triazine (JR99)[4]

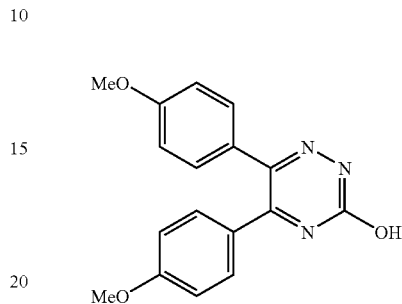

$C_{17}H_{15}N_3O_3$ M=309.32 g/mol

Semicarbazide chlorohydrate (2.22 g, 20 mmol) and sodium acetate (1.80 g, 22 mmol) are added to a solution of 1,2-bis(4-methoxyphenyl)-ethane-1,2-dione (5.4 g, 20 mmol) prepared according to example 1 in acetic acid (25 ml). The mixture is heated at reflux for 12 hours. After returning to ambient temperature, the reaction mixture is poured into water. The raw reaction product is collected by filtration and washed with water. The residue is recrystallized in acetic acid. After filtration and washing in water, 5.9 g (95%) of a yellow solid is obtained after drying. $\delta_H$ (200 MHz, CDCl$_3$), 3.86 (s; 6H), 6.94 (m; 4H), 7.67 (s; 4H).

EXAMPLE 22

Synthesis of 3-chloro-5,6-bis(4-methoxyphenyl)-1,2,4-triazine (JR98)[4]

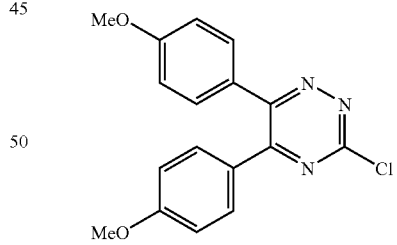

$C_{17}H_{14}N_3O_2$ M=327.77 g/mol

JR99 (4.57 g, 14.8 mmol) prepared according to example 21 in solution in 23 ml of phosphorus oxychloride is brought to reflux for 1.5 hours. The cooled mixture is poured over crushed ice and extracted with diethyl ether. The extract is washed successively with a solution of 2% sodium hydroxide in water until the wash products are neutral. The ether extract is dried on anhydrous sodium sulfate and evaporated. The residue is taken up in ether and filtered. The filtrate is evaporated and yields 3.5 g (72%) of a yellow-brown solid. $\delta_H$ (200 MHz, CDCl$_3$), 3.86 (s; 6H), 6.94 (m; 4H), 7.67 (s; 4H).

BIBLIOGRAPHICAL REFERENCES FOR THE SYNTHESES (1) G. Pitet, H. Cousse, G. Mouzin, *Boll. Chim. Farm.*, 1980, 119, 469
(2) C. Tuzin, M. Ogliaruso, E. I. Becker, *Org. Syn.*, 1961, 41, 3
(3) E. C. Taylor, L. G. French, *J. Org. Chem.*, 1989, 54, 1245
(4) U.S. Pat. No. 3,948,894, 1976

Below are found the physicochemical studies carried out on the compounds which are objects of the present invention, in comparison with the following commercial filters:

PARSOL 1789®:

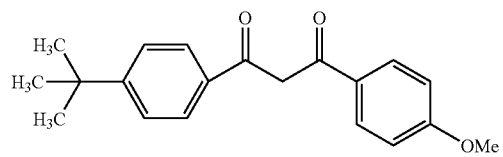

PARSOL MCX®:

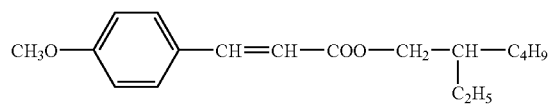

TINOSORB S®:

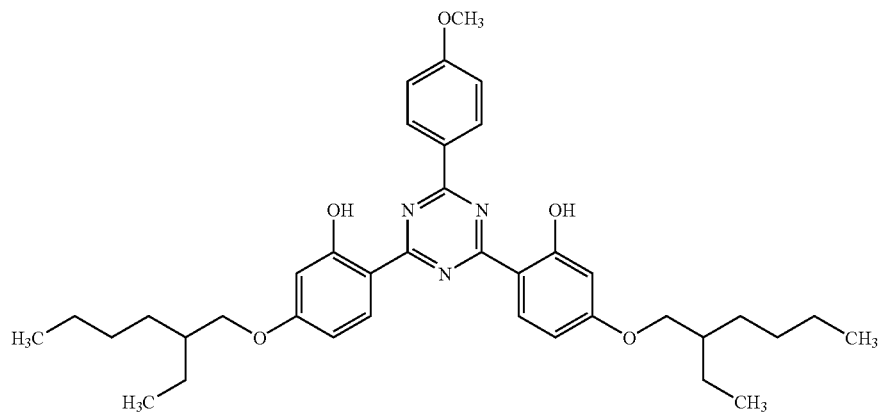

TINOSORB M®:

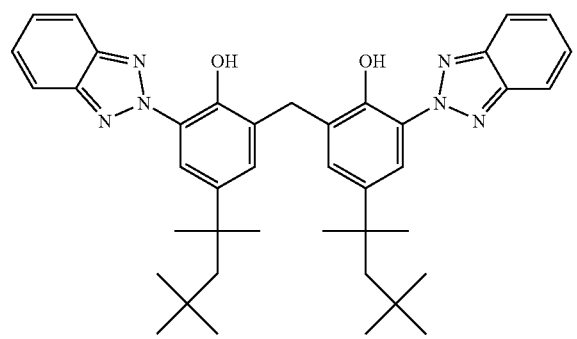

EXAMPLE 23

Spectral Characteristics of the Products: Molar Extinction Coefficient and Specific Absorbance The calculation of the molar extinction coefficient ($\epsilon$) is made from the Beer-Lambert law:

$$\mathrm{Log}_{10}\left(\frac{I_0}{I}\right) = \varepsilon \cdot l \cdot c = A$$

Wherein:
A=absorbance
$I_0$=intensity of the incident light
I=intensity of the transmitted light
$\epsilon$=molar extinction (or molar absorbance) coefficient in $M^{-1} cm^{-1}$
l=path length in cm
c=concentration in mol/l The molar extinction coefficient can be expressed with respect to a given mass of the product. It thus makes it possible to be able to compare the coefficients of extinction between products for the same given quantity. This quantity is 1% by weight. The molar extinction coefficient thus becomes the specific absorbance ($A_{1cm}^{1\%}$).

It is expressed as follows:

$$A_{1\ cm}^{1\%} = \varepsilon \cdot \frac{10}{M}$$

Wherein:
$A_{1cm}^{1\%}$=specific absorbance
$\epsilon$=molar extinction coefficient
M=molar mass The spectral characteristics of the compounds in comparison with commercial filters at a concentration of 10 µg/ml are summarized in tables 2-1 and 2-2.

Procedure: The products are dissolved in ethyl acetate to a concentration of 10 µg/ml. The spectra are measured using a dual-beam spectrophotometer (Varian CARY 50 Scan) between 290 nm and 400 nm.

TABLE 2-1

| Molecules | Maximum molar extinction coefficient | | | | Maximum specific absorbance | | | |
|---|---|---|---|---|---|---|---|---|
| | UVC | UVB | UVA | Visible | UVC | UVB | UVA | Visible |
| PARSOL 1789 ® | 8633 at 275 | | 34100 at 360 | | 278 at 275 | | 1100 at 360 | |
| PARSOL MCX ® | | 24600 at 310 | | | | 848 at 310 | | |
| TINOSORB S ® | | 47150 at 310 | 49580 at 345 | | | 751 at 310 | 789 at 345 | |
| TINOSORB M ® | | 36600 at 305 | 36400 at 345 | | | 556 at 305 | 552 at 345 | |

TABLE 2-2

| | Compounds of formula (I) | | | | | | | |
|---|---|---|---|---|---|---|---|---|
| | Maximum molar extinction coefficient | | | | Maximum specific absorbance | | | |
| Molecules | UVC | UVB | UVA | Visible | UVC | UVB | UVA | Visible |
| JR89 | 19300 at 280 | | 20300 at 335 | | 502 at 280 | | 526 at 335 | |
| JR115 | | 34300 at 310 | | | | 747 at 310 | | |
| JR18 | | 23100 at 290 | | 19000 at 435 | | 591 at 290 | | 483 at 435 |
| JR63 | | 22736 at 295 | | | | 616 at 295 | | |
| JR65 | | 31100 at 315 | | | | 809 at 315 | | |
| JR67 | 26300 at 280 | | 16300 at 330 | | 811 at 280 | | 502 at 330 | |
| JR68 | 22800 at 280 | | 13800 at 330 | | 702 at 280 | | 424 at 330 | |
| JR70 | | 29200 at 310 | | | | 982 at 310 | | |
| JR77 | 19300 at 280 | | 7600 at 360 | | 631 at 280 | | 249 at 360 | |
| JR107 | 25800 at 270 | 27100 at 300 | 19600 at 350 | | 655 at 270 | 688 at 300 | 498 at 350 | |
| JR113 | | 28800 at 295 | 22469 at 340 | | | 721 at 295 | 570 at 340 | |
| JR114 | | | 26000 at 325 | | | | 661 at 352 | |
| JR173 | | 48600 at 305 | | | | 878 at 305 | | |

EXAMPLE 24

The products tested are classified according to spectral distribution in UVA and UVB in a range from 290 nm to 400 nm.

It is possible to differentiate them according to their spectral distribution:

Products with a narrow spectrum:

Products absorbing in the range between 280 nm and 320 nm (UVB)

Products absorbing in the range between 320 nm and 400 nm (UVA)

Products with a broad spectrum:

Products absorbing in UVB (280-320 nm) and UVA-II (380-360 nm)
Products covering UVB and UVA (280-400 nm).

EXAMPLE 24-1

Spectral Distribution of Compounds of Formula (I)

Parsol 1789° only absorbs in UVA (see FIG. 1).

JR18, JR70, JR65 and JR173 absorb in UVB (see FIG. 2).

JR89, JR115, JR63, JR68 and JR77 absorb in UVB (280-320 nm) and UVA-II (280-340 nm) (see FIG. 3).

JR107, JR113, JR114, Tinosorb S® and Tinosorb M® absorb in UVB and UVA (See FIG. 4).

EXAMPLE 24-2

Table 3 summarizes the spectral distributions of the compounds tested.

TABLE 3

| Molecules | UVB 280-320 nm | UVA-II 320-340 nm | UVA-I 340-400 nm | Absorption peaks (nm) |
|---|---|---|---|---|
| Parasol 1789® | | | | 360 |
| WP76 | | | | 290 |
| Parasol® | | | | 310 |
| JR18 | | | | 290 |
| JR65 | | | | 315 |
| JR70 | | | | 310 |
| JR173 | | | | 305 |
| JR89 | | | | 335 |
| JR115 | | | | 310 |
| JR63 | | | | 295 |
| JR68 | | | | 280 and 330 |
| JR70 | | | | |
| JR77 | | | | 310 |
| JR107 | | | | 270-300-350 |
| JR113 | | | | 295 and 340 |
| JR114 | | | | 325 |
| Tinosorb S® | | | | 310 and 345 |
| Tinosorb M® | | | | 305 and 345 |

| | |
|---|---|
| | Very strong absorption |
| | Strong absorption |
| | Average absorption |
| | Weak absorption |
| | No absorption |

EXAMPLE 25

Evaluation of Sun Protection Factor (SPF) In Vitro in a Chemical Solvent or in a Primary Formula The in vitro methods of determining the protective effectiveness of sun products consist of measuring by transmission spectrophotometry the absorption spectrum of the filter in solution or of the product applied on a substrate with the aim of simulating the surface of the skin. The effectiveness against UVB and/or UVA rays, or the effect on the cutaneous response, are then determined by calculation, taking into account or not the UV radiation action spectrum for the damage considered.

EXAMPLE 25-1

Evaluation of Sun Protection Factor (SPF) In Vitro in a Chemical Solvent

The Sayre/Agin and Diffey/Robson method, used since the 1990s, involves a comparative measurement, with the aid of an integrating-sphere spectroradiometer, of the transition from 290 nm to 400 nm in 5 nm steps, the sample being subjected to UV radiation from a stable known source covering the whole of the UV spectrum (unfiltered xenon).

Diffey and Robson evaluate the erythemal response by the following calculation:

$$SPF = \frac{\left(\sum_{290}^{400} E(\lambda) * \varepsilon\right)}{\left(\sum_{290}^{400} \frac{E(\lambda) * \varepsilon}{\overline{MFA(\lambda)}}\right)}$$

$E(\lambda)$=spectral irradiation in $W(m^{-2})(nm^{-1})$ at 40° N sun at 20° zenith angle $\varepsilon$=erythematous capacity $$\overline{MFA(\lambda)} = \frac{\left(\sum_{i=1}^{N} MFA(\lambda)i\right)}{N(\lambda)}$$

$N(\lambda)$=number of values for a given wavelength

The Diffey and Robson formula makes it possible to determine SPF from the measurement of transmittance between 290 nm and 400 nm. Transmittance is measured in solution in ethyl acetate at a concentration of 10 µg/ml using a UV-visible spectrophotometer (Varian CARY 50 Scan).

$$MFA(\lambda) = \frac{1}{T(\lambda)}$$

$T(\lambda)$=transmittance at wavelength $\lambda$

The results of the measurements taken are summarized in table 5.

TABLE 4

In vitro SPF measurement in a chemical solvent

| Molecules | SPF |
|---|---|
| Parsol MCX ® | 20.78 |
| Parsol 1789 ® | 51.1 |
| Tinosorb M ® | 54.07 |
| Tinosorb S ® | 76.19 |
| Compounds of formula (I) | |
| JR65 | 68.21 |
| JR77 | 47.16 |
| JR113 | 67.74 |
| JR173 | 69.02 |

EXAMPLE 25-2

Evaluation of Sun Protection Factor (SPF) In Vitro in a Primary Formula for Mixtures Comprised of Compounds of Formula (Ia) and of Reference Products PMMA (polymethyl methacrylate) plates (50×50 mm, supplied by Europlast) were used.

The dose applied in the in vivo solar product evaluation protocols (2 mg/cm²) is too high for the type of substrate employed here. A study showed that the best correlations with SPF were obtained by the application of 1.2 mg/cm².

Gels were formulated from the triazines that are objects of this invention and certain reference filters. The molecules are solubilized in Transcutol® CG in a water bath. The solution is then placed under magnetic stirring and a gelling agent, Klucel HF (hydroxypropyl cellulose), is added at a concentration of 2%. Stirring is maintained for 30 minutes. SPF is measured using a Labsphere UV-1000 S Transmittance Analyzer spectrophotometer (Labsphere, North Sutton, N.H., USA). The results of the measurements taken are summarized in table 5.

TABLE 5

In vitro SPF measurement in a primary formula

| Mixture | SPF |
|---|---|
| Parsol MCX ® 5% | 17.2 |
| JR65 3% | 10.9 |
| Tinosorb S ® 3% | 9.8 |
| JR65 3% + Tinosorb S ® 3% | 19.4 |
| Parsol MCX ® 5% + JR65 1% | 19.4 |
| Parsol MCX ® 5% + JR67 1% | 27.9 |
| Parsol MCX ® 5% + JR68 1% | 24.1 |
| Parsol MCX ® 5% + JR77 1% | 21.9 |
| Parsol MCX ® 5% + JR113 1% | 18.3 |
| JR65 3% | 9.8 |

EXAMPLE 26

Study of Photostability in Solution in a Chemical Solvent

A Suntest CPS+ (Atlas, Linsengenicht/Altenhasslan, Germany) was used. The Suntest makes it possible to reproduce the solar spectrum and thus to carry out exposures inside at any time without weather constraints.

Setting the MED (minimal erythemal dose):

The radiance of the solar simulator was carefully measured with a spectroradiometer (MSS 2044, Bielefeld, Germany). UVB and UVA intensities were 0.49 mW/cm$^2$ and 6.32 mW/cm$^2$, respectively. The MED value defined by COLIPA is 5.6 J/cm$^2$ in total UV (22). The UV total (UVA+UVB) accounts for 14.8% of the energy delivered by the lamp (power 460 W/m$^2$). An irradiation dose equivalent to 1 MED corresponds to 37.83 J/cm$^2$ (in total spectrum) delivered by the lamp.

The Suntest test duration is calculated using the following formula:

$$t = H/E$$

with:

E=illumination energy in W/m$^2$

H=irradiation dose in J/m$^2$ t=duration of the test in s

The setting of the MED on the Suntest and the correspondence with sun intensity at 3 seaside resorts are indicated in table 6.

TABLE 6

| Sun intensity Location (June 21) | Extreme Agadir | Intense Toulon | Average La Baule |
|---|---|---|---|
| Number of MED/d | 20 | 10 | 5 |
| Dose of corresponding irradiation on the Suntest (in J/m$^2$) | 7566000 | 3783000 | 1891500 |
| Test duration | 4 h 34 min | 2 h 17 min | 1 h 08 min |

Procedure:

The solutions of the compounds are prepared at a concentration of 500 µg/ml in methanol. 50 µl (25 µg) of each solution are deposited in a crystallizer, then irradiated in the Suntest at 5, 10 and/or 20 MED. A non-irradiated control is prepared (deposit of 50 µl of solution and addition of 2.450 ml of methanol). The solvent evaporates during irradiation and the products are taken up in 2.5 ml of methanol. After irradiation, the absorbance of each solution is measured with the UV-visible spectrophotometer (Varian CARY 50 Scan).

The photostability measurement results for the compounds of formula (I) are summarized in table 7.

TABLE 7

| | Photostability at 10 MED | | | Photostability at 20 MED | | |
|---|---|---|---|---|---|---|
| molecule | mean | standard deviation | relative standard deviation | mean | standard deviation | relative standard deviation |
| Parsol 1789 ® | 57.04 | 6.62 | 11.60% | 6.26 | 3.52 | 56.26% |
| Parsol MCX ® | 33.38 | 0.51 | 1.52% | 11.63 | 3.73 | 32.06% |
| JR89 | 97.39 | 2.25 | 2.31% | 98.72 | 1.44 | 1.46% |
| JR115 | 57.63 | 1.04 | 1.81% | 46.42 | 6.39 | 13.76% |
| JR18 | 82.86 | 0.68 | 0.82% | 57.37 | 9.26 | 16.14% |
| JR63 | 62.66 | 2.59 | 4.14% | 39.67 | 3.51 | 8.85% |
| JR65 | 96.91 | 2.26 | 2.33% | 85.5 | 5.81 | 6.80% |
| JR68 | 98.2 | 0.75 | 0.77% | 95.33 | 5.69 | 5.96% |
| JR70 | 44.51 | 2.78 | 6.25% | 30.83 | 5.35 | 17.34% |
| JR77 | 73.03 | 1.72 | 2.36% | 61.14 | 10.52 | 17.20% |
| JR107 | 58.45 | 0.22 | 0.37% | 47.81 | 15.76 | 32.95% |
| JR113 | 98.07 | 1 | 1.02% | 97.67 | 4.04 | 4.14% |
| JR114 | 92.07 | 0.9 | 0.98% | 91.43 | 0.38 | 0.41% |

EXAMPLE 27

Solubility Study

The solubility results for solvents or excipients used in cosmetics are summarized in table 8.

TABLE 8

| Compounds of formula (I) | | |
|---|---|---|
| Molecules | Excipients | Solubility (%) |
| JR65 | Myritol 318 ® | 0.5 |
| | Finsol V NT ® | 1 |
| | Isopropyl adipate | 2 |
| | Butylene glycol | 5 |
| | Hexylene glycol | 5 |
| | Isopropyl myristate | 5 |
| | Cetiol V ® | 2 |
| | Cetiol SN ® | 1 |
| | Arlasolve DMI ® | 8 |
| | PEG400 ® | 5 |
| JR173 | Finsol V NT ® | 7 |
| | PEG400 ® | 2 |

Arlasolve DMI ® = dimethyl isosorbide
Cetiol V ® = cetearyl isononanoate
Cetiol SN ® = decyl oleate
Finsol V NT ® = $C_{12}$-$C_{15}$ alkyl benzoate
Myritol 318 ® = caprylic/capric triglycerides
PEG400 ® = polyethylene glycol (n = 400)

EXAMPLE 28

Formulation Example

| Composition (H/E emulsion) | Quantity (g) |
|---|---|
| Hydrated magnesium sulfate | 0.7 |
| Ethyl hexyl para methoxy cinnamate | 5 |
| JR65 | 8 |
| $C_{12}$-$C_{15}$ alcohol benzoate | 10 |
| Titanium oxide | 3 |
| Triethanolamine | Qs pH 7 |
| Glyceride | 3 |
| Preservatives | Qs |
| Demineralized water | qsp 100 |

The invention claimed is:

1. A method for protecting human skin and/or hair from UV-A and/or UV-B and/or UV-C rays, comprising the application to said human skin and/or hair of an effective amount, of one or more 5,6-diphenyl-1,2,4-triazinic compounds of formula (I):

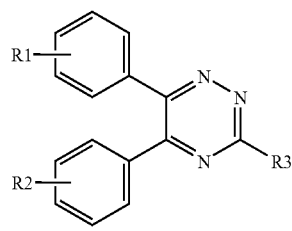

wherein:
the bonds that penetrate into the ring indicate an indifferent substitution position of ortho, meta or para,
$R_1$ and $R_2$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment,
$R_3$ represents a phenyl group optionally substituted 1 to 3 times in ortho, meta or para position with a $C_1$ to $C_{12}$ alkoxy or a cyano.

2. A method for protecting photosensitive materials from UV-A and/or UV-B and/or UV-C rays, comprising the incorporation into said materials or into a filter-layer applied to said materials of one or more 5,6-diphenyl-1,2,4-triazinic compounds of formula (I):

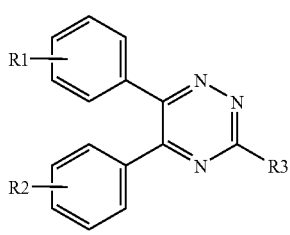

(I)

wherein:
the bonds that penetrate into the ring indicate an indifferent substitution position of ortho, meta or para,
$R_1$ and $R_2$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment,
$R_3$ represents a phenyl group optionally substituted 1 to 3 times in ortho, meta or para position with a $C_1$ to $C_{12}$ alkoxy or a cyano.

3. The method according to claim 2, wherein said materials are selected from the group consisting of plastics, glass and textiles.

4. 5,6-Diphenyl-1,2,4-triazinic compound of formula (Ia):

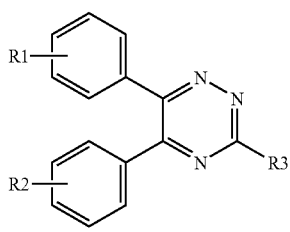

(Ia)

wherein:
$R_1$ and $R_2$ represent a $CH_3O$— group, and
$R_3$ represents:
a phenyl group substituted in ortho, meta or para position by a cyano group.

5. 5,6-Diphenyl-1,2,4-triazinic compounds of formula (Ia) according to claim 4, wherein:
$R_1$ and $R_2$ represent a $CH_3O$— group located in para position, and
$R_3$ represents a phenyl group substituted with a cyano in ortho, meta or para position.

6. 5,6-Diphenyl-1,2,4-triazinic compounds according to claim 4, selected from the group consisting of:
JR107: 3-(4-cyanophenyl)-5,6-bis(4-methoxyphenyl)-1,2,4-triazine
JR113: 3-(3-cyanophenyl)-5,6-bis(4-methoxyphenyl)-1,2,4-triazine
JR114: 3-(2-cyanophenyl)-5,6-bis(4-methoxyphenyl)-1,2,4-triazine
JR144: 3-(3-cyanophenyl)-5,6-diphenyl-1,2,4-triazine
JR145: 3-(2-cyanophenyl)-5,6-diphenyl-1,2,4-triazine.

7. A cosmetic sunscreen composition active in UV-A and/or UV-B and/or UV-C containing an effective quantity of or more 5,6-diphenyl-1,2,4-triazinic compounds of formula (Ia) according to

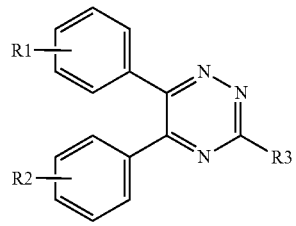

(Ia)

wherein:
$R_1$ and $R_2$ represent a $CH_3O$— group, and
$R_3$ represents:
a phenyl group substituted in ortho, meta or para position by a cyano group,
in combination with a cosmetically acceptable excipient.

8. A cosmetic sunscreen composition according to claim 7, containing in addition one or more sun filters active in UV-A and/or UV-B and/or UV-C.

9. A cosmetic sunscreen composition according to claim 7, wherein the one or more 5,6-diphenyl-1,2,4-triazinic compounds represents between 0.1% and 20% by weight of the total weight of the composition.

* * * * *